US009775571B2

United States Patent
Wei et al.

(10) Patent No.: US 9,775,571 B2
(45) Date of Patent: Oct. 3, 2017

(54) COMPUTED TOMOGRAPHY (CT) IMAGE ACQUISITION DEVICE AND CT SCAN IMAGING SYSTEM WITH G-SHAPED BEAM FOR TWO X-RAY DETECTOR

(75) Inventors: Shiyu Wei, Beijing (CN); Xun Zhu, Beijing (CN); Yixiu Wang, Beijing (CN)

(73) Assignee: Beijing East Whale Image Technology Co., Ltd., Beijing (CN)

( * ) Notice: Subject to any disclaimer, the term of this patent is extended or adjusted under 35 U.S.C. 154(b) by 201 days.

(21) Appl. No.: 14/119,749

(22) PCT Filed: Jun. 8, 2011

(86) PCT No.: PCT/CN2011/075487
§ 371 (c)(1),
(2), (4) Date: Nov. 22, 2013

(87) PCT Pub. No.: WO2012/159279
PCT Pub. Date: Nov. 29, 2012

(65) Prior Publication Data
US 2014/0086384 A1    Mar. 27, 2014

(30) Foreign Application Priority Data
May 23, 2011    (CN) .......................... 2011 1 0134912

(51) Int. Cl.
*A61B 6/00*    (2006.01)
*A61B 6/03*    (2006.01)

(52) U.S. Cl.
CPC ............ *A61B 6/4014* (2013.01); *A61B 6/032* (2013.01); *A61B 6/035* (2013.01); *A61B 6/4007* (2013.01);
(Continued)

(58) Field of Classification Search
CPC ......... A61B 6/032; A61B 6/40; A61B 6/4007; A61B 6/4014
(Continued)

(56) References Cited

U.S. PATENT DOCUMENTS 4,345,158 A * 8/1982 Pfeiler .................. A61B 6/032
378/14
4,994,965 A * 2/1991 Crawford ............... A61B 6/032
324/309
(Continued)

FOREIGN PATENT DOCUMENTS

CN    1517072 A    8/2004
CN    1751661 A    3/2006
(Continued)

OTHER PUBLICATIONS

International Search Report and International Preliminary Report on Patentability/Written Opinion for Application No. PCT/CN2011/075487 dated Jan. 5, 2012.

*Primary Examiner* — Jason McCormack
(74) *Attorney, Agent, or Firm* — Alston & Bird LLP

(57) ABSTRACT

The disclosure provides a Computed Tomography (CT) image acquisition device and a CT scan imaging system. The CT scan imaging system includes: an image acquisition device, which specifically includes a first image acquisition device (1A, 1B) and a second image acquisition device (2A, 2B) that are perpendicular to each other, wherein the first image acquisition device (1A, 1B) or the second image acquisition device (2A, 2B) includes: an X-ray tube (1A, 2A), which is used for emitting X-rays, and a detector (1B, 2B), which is arranged opposite to the X-ray tube in the vertical direction and is used for receiving the X-rays and obtaining projection data according to the X-rays; and an image processing device (4), which is used for acquiring a three-dimensional image through reconstruction of the pro-
(Continued)

jection data, wherein the three-dimensional image includes one or more tomographic images.

14 Claims, 2 Drawing Sheets

(52) U.S. Cl.
CPC .......... *A61B 6/4266* (2013.01); *A61B 6/4405* (2013.01); *A61B 6/4441* (2013.01); *A61B 6/5205* (2013.01)

(58) Field of Classification Search
USPC ............................................. 378/9
See application file for complete search history.

(56) References Cited

U.S. PATENT DOCUMENTS

| | | | |
|---|---|---|---|
| 4,994,985 A * | 2/1991 | Cree et al. ................... | 709/206 |
| 6,198,790 B1 | 3/2001 | Pflaum | |
| 2004/0032927 A1 | 2/2004 | Hoffman | |
| 2005/0089134 A1 | 4/2005 | Bruder et al. | |
| 2005/0116878 A1* | 6/2005 | Warnberg ................ | A61B 6/02 345/1.1 |
| 2005/0175143 A1* | 8/2005 | Miyazaki ............... | A61B 6/032 378/19 |
| 2005/0226363 A1* | 10/2005 | Edie ....................... | A61B 6/032 378/9 |
| 2006/0165213 A1* | 7/2006 | Hambuchen ......... | A61B 6/4441 378/9 |
| 2008/0101530 A1* | 5/2008 | Ullberg ................. | A61B 6/032 378/4 |
| 2009/0129540 A1 | 5/2009 | Bruder et al. | |
| 2010/0014726 A1 | 1/2010 | Schaefer et al. | |
| 2010/0246755 A1* | 9/2010 | Suzuki ................... | A61B 6/032 378/11 |
| 2010/0246756 A1* | 9/2010 | Forthmann ........... | A61B 6/032 378/16 |
| 2010/0310044 A1* | 12/2010 | Manak ................. | A61B 5/6887 378/62 |
| 2011/0268244 A1* | 11/2011 | Handa ................... | A61B 6/022 378/4 |

FOREIGN PATENT DOCUMENTS

| | | |
|---|---|---|
| CN | 1794898 A | 6/2006 |
| CN | 101453950 A | 6/2009 |
| WO | WO 2011030460 A1 * 3/2011 | ............. A61B 6/022 |

* cited by examiner

COMPUTED TOMOGRAPHY (CT) IMAGE ACQUISITION DEVICE AND CT SCAN IMAGING SYSTEM WITH G-SHAPED BEAM FOR TWO X-RAY DETECTOR

FIELD

The disclosure relates to the field of medical apparatus and instruments, and in particular to a Computed Tomography (CT) image acquisition device and a CT scan imaging system.

BACKGROUND

The CT machine according to the existing technology generally is provided with a rotatable scanning frame, of which the inside wall is mounted with an X-ray tube and a detector corresponding to the X-ray tube. By rotating the scanning frame, the projection data of a human body can be acquired in all directions. This X-ray CT machine can acquire X-ray projection data from a human body in all directions by rotating the ray source, thereby reconstructing the projection data to form a tomographic image.

In order to obtain a high-quality tomographic image in a short time, two types of advanced CT machines are provided below at present.

1. CT Machine with Multiple Tubes:

In this CT machine, multiple X-ray tubes and multiple detectors are arranged on one same plane inside the scanning frame, thus the multiple tubes can emit rays simultaneously and the multiple detectors can receive projection data in all directions simultaneously; therefore, both the rotating angle of the scanning frame and the scanning time can be reduced. However, there are certain drawbacks existing in this type of CT machine. Due to the limited thickness of the conventional single-slice linear detector, tomographic image of human body with finite thickness can be acquired only each time, and there are severe limitations in acquiring dynamic images, such as heart images.

2. CT Machine with Multi-Slice Detector:

In order to solve the problem of slice thickness, multi-slice spiral CT appears in recent years. The multi-slice spiral CT technology has made a great breakthrough in the design of detector array, the selection of slice thickness, the reconstruction of algorithm and the improvement of scanning speed, and at present spiral CT machines with 8-slice, 16-slice, 32-slice and 64-slice image have appeared. However, the top number reaches 128 slices only. How to obtain bigger slice thickness remains a problem.

Since the above two CT machines are limited by the pixel size of the array unit of the detector, it is very difficult to achieve a higher spatial resolution, worse, the conversion rate of ray is low and the radiation dose is strong. In addition, existing CT machines are huge in size and are immovable, and the person who accepts physical examination must go to the fixed CT room, thus the usage is limited and the construction of CT room adds the cost to certain extent.

At present, no solution has been proposed in view of the problem existing in related art that the CT machine can not image in real time and is low in imaging efficiency and high in production cost.

SUMMARY

Since no solution has been proposed in view of the problem existing in related art that the CT machine can not image in real time and is low in imaging efficiency and high in production cost, the main purpose of the disclosure is to provide a CT image acquisition device and a CT scan imaging system to solve the above problem.

In order to achieve the above purpose, according to one aspect of the disclosure, a CT image acquisition device is provided, including: a first image acquisition device, which includes: a first X-ray tube, which is used for emitting horizontal X-rays; and a first detector, which is arranged opposite to the first X-ray tube in the vertical direction and is used for receiving the horizontal X-rays and obtaining projection data according to the horizontal X-rays; a second image acquisition device, which includes: a second X-ray tube, which is used for emitting vertical X-rays; and a second detector, which is arranged opposite to the second X-ray tube in the vertical direction and is used for receiving the vertical X-rays and obtaining projection data according to the vertical X-rays.

In order to achieve the above purpose, according to another aspect of the disclosure, a CT scan imaging system is provided, including: an image acquisition device, which is used for acquiring projection data and includes: a first image acquisition device and a second image acquisition device which are perpendicular to each other, wherein the first image acquisition device or the second image acquisition device includes: an X-ray tube, which is used for emitting X-rays; a detector, which is arranged opposite to the X-ray tube in the vertical direction and is used for receiving the X-rays and obtaining the projection data according to the X-rays; and an image processing device, which is used for acquiring a three-dimensional image through reconstruction of the projection data, wherein the three-dimensional image includes one or more tomographic images.

In the disclosure, an image acquisition device is adopted, which is used for acquiring projection data and includes: a first image acquisition device and a second image acquisition device which are perpendicular to each other, wherein the first image acquisition device or the second image acquisition device includes: an X-ray tube, which is used for emitting X-rays, and a detector, which is arranged opposite to the X-ray tube in the vertical direction and is used for receiving the X-rays and obtaining projection data according to the X-rays; and an image processing device, which is used for reconstructing the projection data to acquire a three-dimensional image, wherein the three-dimensional image includes one or more tomographic images. Thus, the problem existing in related art that the CT machine can not image in real time and is low in imaging efficiency and high in production cost is solved, and the CT machine can image in real time quickly and has a low cost.

BRIEF DESCRIPTION OF THE DRAWINGS

For a better understanding of the disclosure, accompanying drawings described hereinafter are provided to constitute one part of the application; the schematic embodiments of the disclosure and the description thereof are used to illustrate the disclosure but to limit the disclosure improperly. In the accompanying drawings.

DETAILED DESCRIPTION OF THE EMBODIMENTS

It should be noted that the embodiments in the application and the characteristics of the embodiments can be combined if no conflict is caused. The disclosure is described below in detail by reference to the accompanying drawings in conjunction with embodiments.

Figure 1:
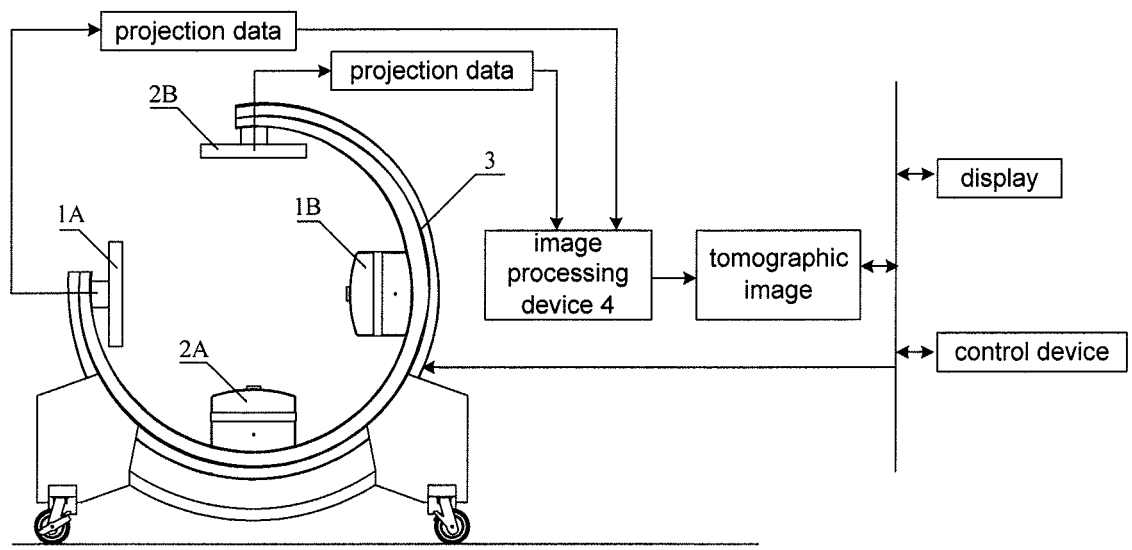
FIG. 1 shows a structure diagram of a CT scan imaging system according to the embodiment of the disclosure.

FIG. 1 shows a structure diagram of a CT scan imaging system according to the embodiment of the disclosure. As shown in FIG. 1, the CT scan imaging system includes: an image acquisition device and an image processing device 4.

The image acquisition device is used for acquiring projection data and may include: a first image acquisition device 1A and 1B and a second image acquisition device 2A and 2B which are perpendicular to each other, wherein the first image acquisition device or the second image acquisition device includes: an X-ray tube, which is used for emitting X-rays; a detector, which is arranged opposite the X-ray tube in the vertical direction and is used for receiving the X-rays and obtaining projection data according to the X-rays; and the image processing device (4), which is used for acquiring a three-dimensional image through reconstruction of the projection data, wherein the three-dimensional image includes one or more tomographic images.

The first image acquisition device referred in the above embodiment of the disclosure may include: a first X-ray tube 1A, which is used for emitting horizontal X-rays; a first detector 1B, which is arranged opposite to the first X-ray tube 1A in the vertical direction and is used for receiving the horizontal X-rays and obtaining projection data according to the horizontal X-rays. The second image acquisition device may include: a second X-ray tube 2A, which is used for emitting vertical X-rays; a second detector 2B, which is arranged opposite to the second X-ray tube 2A in the vertical direction and is used for receiving the vertical X-rays and obtaining projection data according to the vertical X-rays. The scan area of both the first image acquisition device and the second image acquisition device is half the full scanning angle.

In the embodiment shown in FIG. 1, the CT scan imaging system acquires the projection data of a human body through four components, that is, two sets of X-ray tubes and two sets of flat panel detectors, and performs CT reconstruction based on the projection data to obtain tomographic images of the human body. Since this device has two sets of image acquisition devices, that is, two sets of transmitting and receiving devices, the scanning angle can be reduced by half and thus the scanning time is reduced, therefore, the CT machine can image in real time quickly, moreover, since the number of transmitting and receiving devices is reduced, the cost is reduced too. In addition, the whole device is moveable, which can be used in an operating room, an intensive care unit and other places, thus there exist no need to move the patients.

As shown in FIG. 1, the image acquisition device involved in this application is mounted on the inside wall of a G-shaped beam 3, wherein the G-shaped beam 3 is an annular body with a quarter of opening and is rotatable. Each image acquisition device includes an X-ray tube and a detector.

Specifically, the two X-ray tubes and the two detectors involved in the embodiment of this application, as two sets of transmitting and receiving devices, may be mounted on the upper and lower relative positions, the left and right relative positions respectively. When X-rays are emitted, the two X-ray tubes and the two detectors rotate simultaneously to acquire projection data of one same section in all directions, thereby reducing the scanning rotating angle of the conventional CT machine by half and thus shortening the scanning time. The two sets of transmitting and receiving devices can realize bidirectional real-time acquisition and can display image in real time, with frame frequency reaching more than 25 frames per second. Preferably, the system of this application includes at least one display, which is used for displaying a three-dimensional image. One, two or more displays may be selected to display image depending on the actual working environment.

The detector referred in FIG. 1 might be a flat panel detector, wherein each row of pixels of this flat panel detector might be viewed as a layer of array detectors; generally, the flat panel detector has thousands of rows, which greatly increases the layer number of the detectors. In this application, the pixel size of the flat panel detector is smaller than the pixel size of common detectors, enabling an improvement of spatial resolution. Moreover, the high conversion rate of X-ray of the flat panel detector in this application contributes to the reduction of radiation dose. Further, the short reading time and the fast reading speed make dynamic CT imaging of heart like available.

The working principle of the flat panel detector applied in this application is as follows: when there is an X-ray emitted to the scintillation crystal layer of the detector, the X-ray photon energy is converted into visible-light photon emission; then the visible light excites the photodiode to generate current, and the current integrates on the compactor of the photodiode to form stored charges, wherein the stored charge quantity of each pixel and the photon energy of the incident X-ray within the corresponding charge quantity scope is in positive proportion to the quantity of charges; and finally the analogue electric signal is converted into a digital signal through A/D. This digital signal is the projection data of a section of a human body.

Preferably, the G-shaped beam adopted in this application is far less than the conventional CT scanning cabin in thickness, with characteristics of small size and mobility, thus it can be applied to an operating room. In addition, there is no need to set up a special CT room, thus cost is reduced.

The embodiment of the disclosure is described below in detail by reference to FIG. 1. As shown in FIG. 1, X-ray tubes 1A, 2A emit X-rays, which are detected by the flat panel detectors 1B, 2B arranged at corresponding positions after passing through a human body located at the central position of the G-shaped beam, a motor drives the G-shaped beam to rotate at a constant speed; the flat panel detectors 1B, 2B input the projection data of a section of the human body detected in all directions to the image processing device 4, which then performs CT reconstruction based on this series of projection data to obtain tomographic images of the section of the human body and thus reconstructs out a three-dimensional image of the human body.

Preferably, the image acquisition device referred in the above embodiment can further include: a driving device, which is used for receiving a control signal from external equipment, through which the G-shaped beam is driven to rotate at a constant speed in a predetermined direction. Specifically, the G-shaped beam can rotate clockwise or anticlockwise. Further, a moveable device, for example, rolling wheel, can be arranged at the bottom of the G-shaped beam, for the convenience of movement.

In the embodiment of this application, a control device is adopted to generate the control signal, which is used to control the image acquisition device in the G-shaped beam 3 to rotate clockwise or anticlockwise to obtain projection data multi-directionally. That is to say, the control device drives the G-shaped beam to rotate at a constant speed, specifically, the control device may include a control panel, which is used for receiving an operation from a user to generate the control signal, then the system controls, through the control signal, the image acquisition device to rotate by one degree per second clockwise or anticlockwise, and the operation executed by the user via the control panel can be displayed on a monitor or stored in a computer.

Figure 2:
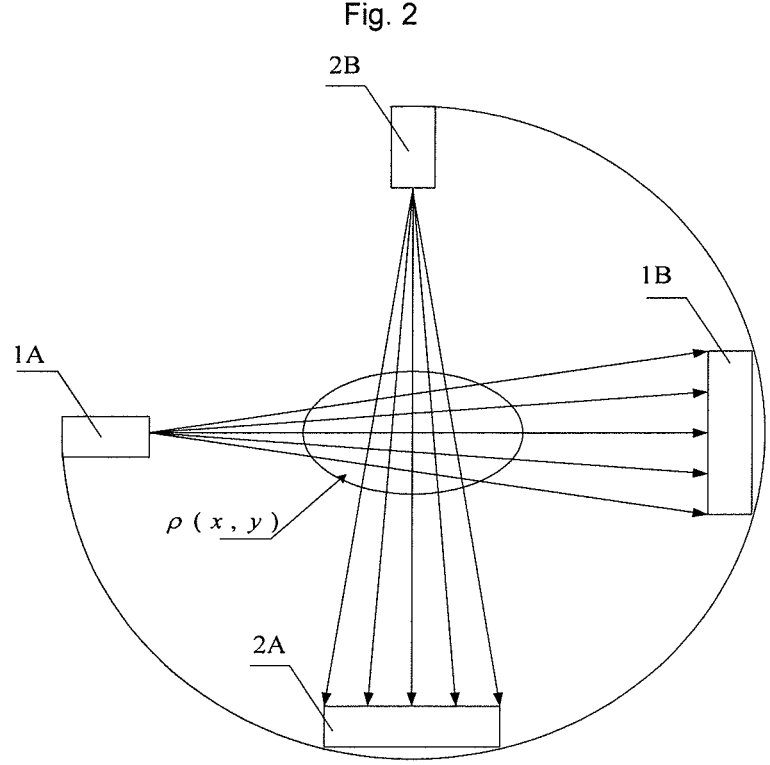
FIG. 2 shows a diagram of reconstruction of projection data based on the CT scan imaging system shown in FIG. 1.

In this application, in order to obtain one or more tomographic images of a human body acquired by the detector, it is needed to reconstruct the projection data through certain reconstruction algorithm. As shown in FIG. 2, given $\rho(x,y)$ is the tomographic image of a section. First, we can measure the total attenuation coefficient b of each beam of X-rays projected onto the flat panel detector after passing through the human body; and the elements on the path through which each beam of X-rays passes compose a matrix A, here, the matrix A, the total attenuation coefficient b and the tomographic image $\rho(x,y)$ have the following relationship: A $\rho(x,y)=b$, therefore, the tomographic image $\rho(x,y)$ can be obtained through calculation.

Figure 3:
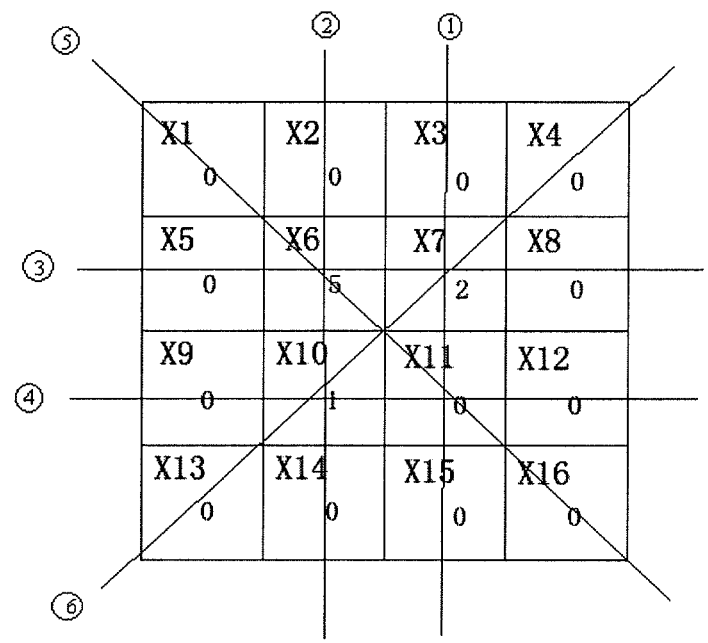
FIG. 3 shows a diagram of a reconstruction algorithm based on the CT scan imaging system shown in FIG. 1.

Specifically, as shown in FIG. 3, the X-ray tube emits six X-rays to pass through the human body, and the total attenuation coefficient can be measured on the detector as b=[2, 6, 7, 1, 5, 3], the value of the element with X-ray passing through is set to 1, while the value of the element without X-ray passing through is set to 0; thus, the matrix A can be obtained as follows:

$$\begin{bmatrix} 0 & 0 & 1 & 0 & 0 & 0 & 1 & 0 & 0 & 0 & 1 & 0 & 0 & 0 & 1 & 0 \\ 0 & 1 & 0 & 0 & 0 & 1 & 0 & 0 & 0 & 1 & 0 & 0 & 0 & 1 & 0 & 0 \\ 0 & 0 & 0 & 0 & 1 & 1 & 1 & 1 & 0 & 0 & 0 & 0 & 0 & 0 & 0 & 0 \\ 0 & 0 & 0 & 0 & 0 & 0 & 0 & 0 & 1 & 1 & 1 & 1 & 0 & 0 & 0 & 0 \\ 1 & 0 & 0 & 0 & 0 & 1 & 0 & 0 & 0 & 0 & 1 & 0 & 0 & 0 & 0 & 1 \\ 0 & 0 & 0 & 1 & 0 & 0 & 1 & 0 & 0 & 1 & 0 & 0 & 1 & 0 & 0 & 0 \end{bmatrix};$$

take the parameters into the formula A $\rho(x,y)=b$ to obtain:

$$\begin{bmatrix} 0 & 0 & 1 & 0 & 0 & 0 & 1 & 0 & 0 & 0 & 1 & 0 & 0 & 0 & 1 & 0 \\ 0 & 1 & 0 & 0 & 0 & 1 & 0 & 0 & 0 & 1 & 0 & 0 & 0 & 1 & 0 & 0 \\ 0 & 0 & 0 & 0 & 1 & 1 & 1 & 1 & 0 & 0 & 0 & 0 & 0 & 0 & 0 & 0 \\ 0 & 0 & 0 & 0 & 0 & 0 & 0 & 0 & 1 & 1 & 1 & 1 & 0 & 0 & 0 & 0 \\ 1 & 0 & 0 & 0 & 0 & 1 & 0 & 0 & 0 & 0 & 1 & 0 & 0 & 0 & 0 & 1 \\ 0 & 0 & 0 & 1 & 0 & 0 & 1 & 0 & 0 & 1 & 0 & 0 & 1 & 0 & 0 & 0 \end{bmatrix} \bullet \begin{bmatrix} X_1 \\ X_2 \\ X_3 \\ X_4 \\ X_5 \\ X_6 \\ X_7 \\ X_8 \\ X_9 \\ X_{10} \\ X_{11} \\ X_{12} \\ X_{13} \\ X_{14} \\ X_{15} \\ X_{16} \end{bmatrix} = \begin{bmatrix} 2 & 6 & 7 & 1 & 5 & 3 \end{bmatrix}$$

that is, $$P_1 = X_3 + X_7 + X_{11} + X_{15} = 2$$

$$P_2 = X_2 + X_6 + X_{10} + X_{14} = 6$$

$$P_3 = X_5 + X_6 + X_7 + X_8 = 7$$

$$P_4 = X_9 + X_{10} + X_{11} + X_{12} = 1$$

$$P_5 = X_1 + X_6 + X_{11} + X_{16} = 5$$

$$P_6 = X_4 + X_7 + X_{10} + X_{13} = 3$$

Then, based on the back projection algorithm:

$$X_1 = P_5 = 5$$

$$X_{10} = P_2 + P_4 + P_6 = 10$$

...

$X_1 \ldots X_{16}$ are calculated finally, that is, tomographic image $\rho(x,y)$ is obtained.

In the above embodiment, the back projection algorithm is adopted during the reconstruction of the projection data. The density value of any point on the section plane can be viewed as the average of the sum of the projection value of all rays passing through this point on this plane. The projection data of certain angle is applied to the entire space along the reverse direction of the projection direction to obtain a two-dimensional distribution, which is a reconstructed image similar to the original image.

To sum up, the outstanding feature of the G-shaped beam CT device in the preferred embodiment is that: through certain reconstruction algorithm, a common G-shaped beam X-ray machine can perform scan to obtain the tomographic image that can be obtained by a CT machine only, thereby reconstructing out a three-dimensional image of a human body.

Figure 4:
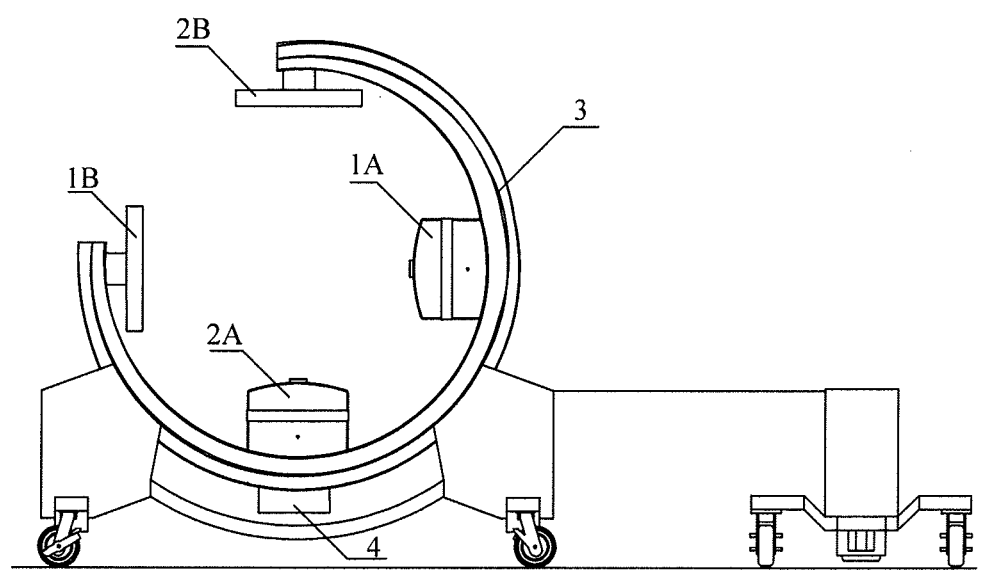
FIG. 4 shows a structure diagram of a CT image acquisition device according to one embodiment of the disclosure.

FIG. 4 shows a structure diagram of a CT image acquisition device according to the embodiment of the disclosure. As shown in FIG. 4, the CT-image acquisition device includes: a first image acquisition device and a second image acquisition device, in which, the first image acquisition device may include: a first X-ray tube 1A, which is used for emitting horizontal X-rays; a first detector 1B, which is arranged opposite to the first X-ray tube 1A in the vertical direction and is used for receiving the horizontal X-rays and obtaining projection data according to the horizontal X-rays; the second image acquisition device may include: a second X-ray tube 2A, which is used for emitting vertical X-rays; a second detector 2B, which is arranged opposite to the second X-ray tube 2A in the vertical direction and is used for receiving the vertical X-rays and obtaining projection data according to the vertical X-rays.

The CT image acquisition device in this application further includes a G-shaped beam, of which the inside wall is mounted with the first image acquisition device and the second image acquisition device, wherein the G-shaped beam is an annular body with a quarter of opening, and the orthocentre where the first image acquisition device is perpendicularly intersected with the second image acquisition device is overlapped with the centre of the annular body.

In the above embodiment of this application, the four components, that is, two sets of X-ray tubes and two sets of flat panel detectors, might be uniformly distributed on the G-shaped beam, to form two sets of X-ray sources and receiving systems that are perpendicular to each other, the G-shaped beam can rotate along a shaft by big angles to acquire projection data in all directions, and reconstruct this series of projection data to obtain tomographic images of a human body. Thus, a common G-shaped beam X-ray machine can obtain tomographic images through a reconstruction algorithm. Moreover, since the two sets of transmitting and receiving devices (two sets of X-ray tubes and two sets of flat panel detectors) can reduce the scanning angle by half, therefore, the scanning time is reduced.

Preferably, the CT image acquisition device in this application can further include a driving device 4, which is used for receiving from external equipment a control signal, through which the G-shaped beam 3 is driven to rotate at a constant speed in a predetermined direction the direction includes clockwise direction or anticlockwise direction.

Further, the whole device in this application is provided with a rolling wheel at the bottom, thus the device is moveable and can be directly pushed to an operating room, an intensive care unit and other places to be used, therefore, patients have no need to move.

As for the CT image acquisition device shown in FIG. 4, since the biggest length is 1960 mm and the biggest width is 800 mm, which occupies small area, there is no need to set up a special CT room to store the CT machine and the cost is reduced; moreover, since there are four rolling wheels arranged at the bottom of the G-shaped beam, the CT image acquisition device is convenient to be moved and can be directly pushed to an operating room or an intensive care room to be used, thus patients have no need to move.

From the above description, it can be seen that the disclosure achieves the following technical effects: the device includes two sets of X-ray tubes and two sets of flat panel detectors, and a rotatable G-shaped beam, wherein the G-shaped beam can rotate by big angles around a shaft, thereby acquiring projection data multi-directionally from two directions simultaneously to reconstruct tomographic images of a human body, thus the scanning time is reduced and the imaging efficiency is improved. Since the pixel size of the flat panel detector is far less than the pixel size of the conventional CT detector, the image has a better spatial resolution, since the ray has a high conversion rate, a reduction is achieved in radiation dose, and since the reading speed is fast, the device is applicable to dynamic imaging of heart. Meanwhile, since the whole device, with rolling wheels arranged at the bottom, is moveable, the system can be directly pushed to an operating room, an intensive care room and other places to be used.

Obviously, those skilled in the art should understand that the modules or steps described above can be implemented by a common computer device; the modules or steps can be integrated on a single computing device or distributed on a network composed of a plurality of computing devices; optionally, the modules or steps can be implemented by a programming code executable by a computing device, thus they can be stored in a storage device to be executed by a computing device, or manufactured into individual integrated circuit module respectively, or several of them can be manufactured into a single integrated circuit module to implement; in this way, the disclosure is not limited to any combination of specific hardware and software.

The above are only the preferred embodiments of the disclosure and not intended to limit the disclosure. For those skilled in the art, various modifications and changes can be made to the disclosure. Any modification, equivalent substitute and improvement made within the spirit and principle of the disclosure are deemed to be included within the scope of protection of the disclosure.

What is claimed is:

1. A Computed Tomography (CT) image acquisition device, comprising:
    a first image acquisition device, comprising:
        a first X-ray tube, configured to emit horizontal X-rays; and
        a first detector, arranged opposite to the first X-ray tube in the horizontal direction and configured to receive the horizontal X-rays and obtain projection data according to the horizontal X-rays;
    a second image acquisition device, comprising:
        a second X-ray tube, configured to emit vertical X-rays; and
        a second detector, arranged opposite to the second X-ray tube in the vertical direction and configured to receive the vertical X-rays and obtain projection data according to the vertical X-rays;
    the first detector and the second detector are flat panel detectors, wherein each row of pixels of the flat panel detectors is viewed as a layer of array detectors, and the pixels are configured to store charge quantity;
    wherein, when there is an X-ray emitted to a scintillation crystal layer of the first detector or the second detector, wherein the first detector and the second detector both comprise the scintillation crystal layer and a photodiode, and wherein the photodiode comprises a compactor, the X-ray photon energy is converted into visible-light photon emission; then the visible light excites the photodiode to generate current, and the current integrates on the compactor of the photodiode to form stored charges, wherein the stored charge quantity of each pixel is in positive proportion to the photon energy and quantity of the incident X-ray within a corresponding pixel scope of each pixel; and an analogue electric signal is converted into a digital signal through A/D, the digital signal is the projection data;
    wherein the two X-ray tubes and the two detectors, as two sets of transmitting and receiving devices, realize bidirectional real-time acquisition and display image series in real time, with frame frequency reaching more than 25 frames per second;
    the device further comprising:
    a G-shaped beam, of which the inside wall is mounted with the first image acquisition device and the second image acquisition device, wherein the G-shaped beam is an annular body with a quarter of opening, and the intersection of the first image acquisition device and the second image acquisition device, perpendicular to each other, is overlapped with the centre of the annular body.

2. The device according to claim 1, further comprising: a driving device, configured to receive a control signal from an external equipment, through which the G-shaped beam is driven to rotate at a constant speed in a predetermined direction.

3. A Computed Tomography (CT) scan imaging system, comprising:
    an image acquisition device, configured to acquire projection data and comprising: a first image acquisition device and a second image acquisition device which are perpendicular to each other, wherein the first image acquisition device or the second image acquisition device comprises:
an X-ray tube, configured to emit X-rays, wherein the X-ray tube comprises a first X-ray tube or a second X-ray tube, wherein the first X-ray tube is configured to emit horizontal X-rays, and wherein the second X-ray tube is configured to emit vertical X-rays;
a detector, arranged opposite to the X-ray tube in the vertical direction and configured to receive the X-rays and obtain the projection data according to the X-rays, wherein the detector comprises a first detector or a second detector, wherein the first detector is arranged opposite to the first X-ray tube in the horizontal direction and is configured to receive the horizontal X-rays, and wherein the second detector is arranged opposite to the second X-ray tube in the vertical direction and is configured to receive the vertical X-rays; and
an image processing device, configured to acquire a three-dimensional image through reconstruction of the projection data, wherein the three-dimensional image comprises one or more tomographic images;
wherein the first image acquisition device comprises the first detector, the second image acquisition device comprises the second detector, the first detector and the second detector are flat panel detectors, wherein each row of pixels of the flat panel detectors is viewed as a layer of array detectors, and the pixels are configured to store charge quantity;
wherein when there is an X-ray emitted to a scintillation crystal layer of the first detector or the second detector, wherein the first detector and the second detector both comprise the scintillation crystal layer and a photodiode, and wherein the photodiode comprises a compactor, the X-ray photon energy is converted into visible-light photon emission; then the visible light excites the photodiode to generate current, and the current integrates on the compactor of the photodiode to form stored charges, wherein the stored charge quantity of each pixel is in positive proportion to the photon energy and quantity of the incident X-ray within a corresponding pixel scope of each pixel; and an analogue electric signal is converted into a digital signal through A/D, the digital signal is the projection data;
wherein the two X-ray tubes and the two detectors, as two sets of transmitting and receiving devices, realize bidirectional real-time acquisition and display image series in real time, with frame frequency reaching more than 25 frames per second;
the system further comprising: a G-shaped beam, of which the inside wall is mounted with the image acquisition device, wherein the G-shaped beam is an annular body with a quarter of opening.

4. The system according to claim 3, further comprising:
a control device, configured to generate a control signal, through which the G-shaped beam is driven to rotate at a constant speed in a predetermined direction to obtain the projection data in all directions.

5. The system according to claim 3, wherein the control device further comprises: a control panel, configured to receive an operation from a user to generate the control signal, wherein the control signal controls the image acquisition device to rotate by one degree per second.

6. The system according to claim 3, wherein the image processing device comprises:
a computation device, configured to acquire the tomographic image $\rho(x,y)$ according to a formula $A\rho(x,y)=b$, where A represents an element matrix obtained when multiple rays of any one beam of X-rays pass through a human body, and b represents an attenuation coefficient, wherein the projection data includes the element matrix and the attenuation coefficient.

7. The system according to claim 5, further comprising: at least one display, configured to display the three-dimensional image.

8. The system according to claim 3, wherein the image acquisition device further comprises: a driving device, configured to receive from an external equipment a control signal, through which the G-shaped beam is driven to rotate at a constant speed in a predetermined direction.

9. The system according to claim 3, wherein the detector is a flat panel detector, and the scan area of both the first image acquisition device and the second image acquisition device is half the full scanning angle.

10. The system according to claim 3, further comprising: a moveable device, arranged at the bottom of the G-shaped beam.

11. The system according to claim 3, wherein the length of the G-shaped beam is not greater than 1960 mm, and the width is not greater than 800 mm.

12. The system according to claim 3, wherein the image processing device comprises:
a computation device, configured to acquire the tomographic image $\rho(x,y)$ according to a formula $A\rho(x,y)=b$, where A represents an element matrix obtained when multiple rays of any one beam of X-rays pass through a human body, and b represents an attenuation coefficient, wherein the projection data includes the element matrix and the attenuation coefficient.

13. The system according to claim 3, wherein the image processing device comprises:
a computation device, configured to acquire the tomographic image $\rho(x,y)$ according to a formula $A\rho(x,y)=b$, where A represents an element matrix obtained when multiple rays of any one beam of X-rays pass through a human body, and b represents an attenuation coefficient, wherein the projection data includes the element matrix and the attenuation coefficient.

14. The system according to claim 4, wherein the image processing device comprises:
a computation device, configured to acquire the tomographic image $\rho(x,y)$ according to a formula $A\rho(x,y)=b$, where A represents an element matrix obtained when multiple rays of any one beam of X-rays pass through a human body, and b represents an attenuation coefficient, wherein the projection data includes the element matrix and the attenuation coefficient.

* * * * *